United States Patent
Kumbrandt et al.

(10) Patent No.: US 8,119,415 B2
(45) Date of Patent: Feb. 21, 2012

(54) X-RAY FLUORESCENCE METHOD FOR A COMPOSITION ANALYSIS OF A SAMPLE CONTAINING AT LEAST TWO ELEMENTS

(75) Inventors: Lars Kumbrandt, Orsundsbro (SE); Johan Malmqvist, Skelleftea (SE)

(73) Assignee: Multiscat AB, Orsundsbro (SE)

( * ) Notice: Subject to any disclaimer, the term of this patent is extended or adjusted under 35 U.S.C. 154(b) by 659 days.

(21) Appl. No.: 12/298,685

(22) PCT Filed: Apr. 17, 2007

(86) PCT No.: PCT/SE2007/050240
§ 371 (c)(1), (2), (4) Date: Oct. 27, 2008

(87) PCT Pub. No.: WO2007/126371
PCT Pub. Date: Nov. 8, 2007

(65) Prior Publication Data
US 2009/0177411 A1    Jul. 9, 2009

(30) Foreign Application Priority Data
Apr. 28, 2006 (SE) ...................................... 0600946

(51) Int. Cl.
*G01N 21/76* (2006.01)
(52) U.S. Cl. ........ 436/172; 436/164; 436/165; 436/166; 436/171

(58) Field of Classification Search .................. None
See application file for complete search history.

(56) References Cited

FOREIGN PATENT DOCUMENTS
EP    0 400 396    5/1990

OTHER PUBLICATIONS

International Search Report filed dated Jul. 13, 2007, filed in PCT Application.
Malmqvist, J. "Application of J. E. Fernandez algorithms in the evaluation of X-ray intensities measured on fused glass discs for a set of International standards and a proposed calibration procedure", X-Ray Spectrometry 2001, vol. 30, p. 83-92.

*Primary Examiner* — Yelena G Gakh
(74) *Attorney, Agent, or Firm* — Young & Thompson

(57) ABSTRACT

Process of placing a sample of known concentrations of known elements in a spectrometer; measuring the intensity I1, I2 . . . In of the different elements included in the sample, by relating known concentrations C1, C2 . . . Cn for the elements included in the sample to the measured intensities I1, I2 . . . In so as to calculate a fictive intensity for a 100%-pure element for each of the elements included; calculating calibration constants K1, K2 . . . Kn for each of the elements as the relationship between measured intensity I1, I2 . . . In and the calculated intensity of respective 100%-pure elements; placing a sample of unknown concentrations of the elements in the spectrometer and reading-off the intensity of the different elements; and calculating the concentration of respective elements in the last mentioned sample as the measured intensity multiplied by respective calibration constants for the elements present in the sample.

4 Claims, 1 Drawing Sheet

| 7 | Ident | Date | SI | FE | B | LI | OO | RT | T | Q |
|---|-------|------|-----|------|-------|-------|-------|-------|-------|-------|
| 1 | FE1001 | 60411 | 0.41 | 100.01 | 17.42 | 11.19 | 58.21 | 0.00 | 0.00 | 0.00 |
| 2 | SI1001 | 60411 | 100.01 | 0.04 | 17.44 | 11.20 | 61.96 | -0.01 | -0.01 | -0.00 |
| 3 |  | 60412 |  |  |  |  |  |  |  |  |
| 4 | FESI | 60411 | 49.36 | 52.35 | 17.38 | 11.16 | 59.97 | -0.01 | -1.72 | 0.28 |
| 5 |  | 60412 |  |  |  |  |  |  |  |  |
| 6 | FE1001 | 60412 | 0.01 | 100.91 | 17.41 | 11.18 | 58.17 | -0.00 | 0.00 | 0.00 |
| 7 | SI1001 | 60412 | 97.67 | 0.04 | 17.52 | 11.25 | 61.99 | 0.01 | 2.33 | -0.39 |

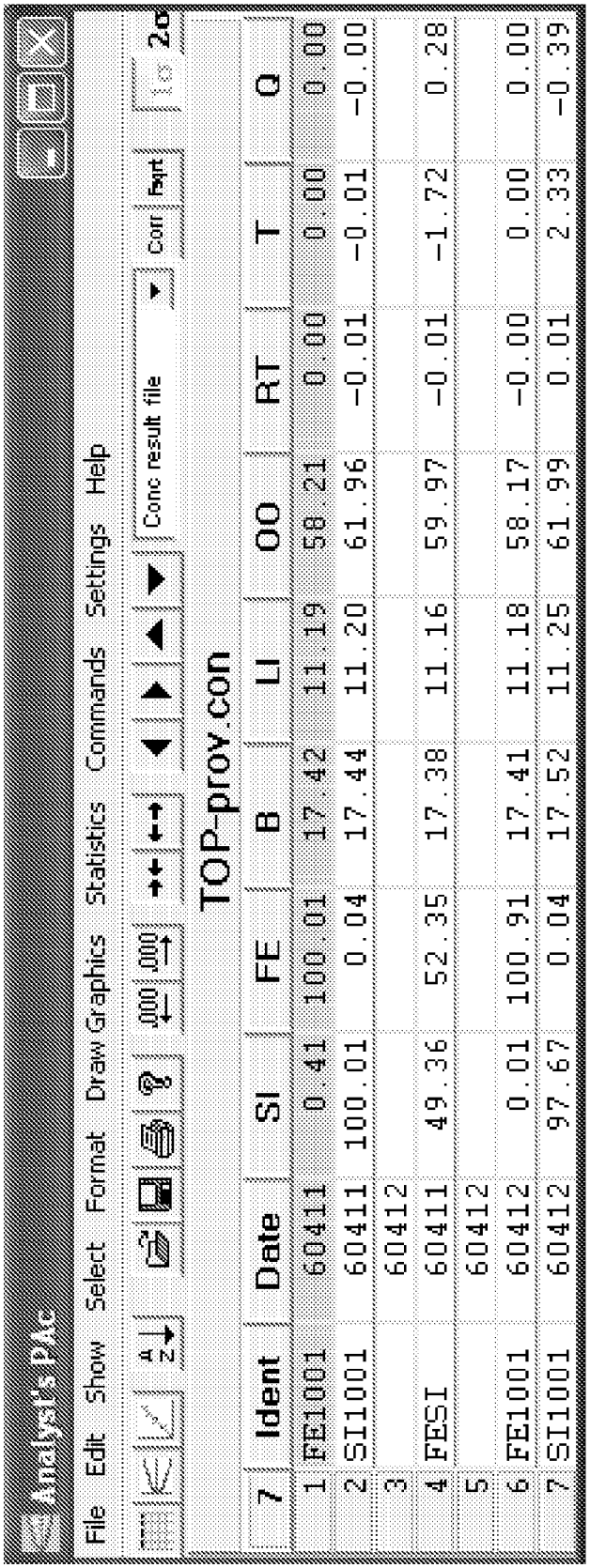

X-RAY FLUORESCENCE METHOD FOR A COMPOSITION ANALYSIS OF A SAMPLE CONTAINING AT LEAST TWO ELEMENTS

The present invention relates to a calibration process in X-ray fluorescence analysis with the aid of solely one sample.

BACKGROUND OF THE INVENTION

Present day X-spectrometers are highly developed with many facilities for facilitating the calibration of instrument parameters and the registration of measurements. In all chemical analytical processes the calibration of the instrument to be used is both time consuming and an important part of the process. This applies, for instance, to the calibration of the parameters of the instrument used, the supervision of the calibrations made, or in other words the control of the operational reliability of the instrument used and, not least, the work involved in the validation of the chemical analytical process that has been developed and its documentation. The process proposed enables the work involved to be greatly simplified and the process by which this can be achieved will be described hereinafter for a simple case in which X-ray fluorescence analysis has been applied.

All chemical-analytical methods are based on some physical-chemical property of an element which shall be characterized by measuring this property or established in some other way. In addition, it is necessary in the majority of cases also to determine a background, the reason for which background is often unknown. In other words, it is necessary to establish when calibrating an element at least two properties (two points). This also applies to determining the concentration of the element with respect to a standard that is used in the validation of an analytical process.

A calibration is thus usually carried out with the aid of one or more samples per element with the subsequent determination/measurement of the background of the element concerned.

A method of how calibration of an element can be carried out with the aid of a glass standard containing a "highly pure" chemical has been described in an earlier article by the inventor, "Application of J. E. Fernández algorithms in the evaluation of X-ray intensities measured on fused glass discs for a set of international standards and a proposed calibration procedure", J. Malmqvist; X-RAY SPECTROMETRY; X-Ray Spectrom 2001; 30:83-92. Thus, in the case mentioned there is required one standard for each element to be calibrated. This article shall be included as a part of the present application.

The present invention solves the problem mentioned above.

SUMMARY OF THE INVENTION

The present invention thus relates to a method of analysing a sample spectrometrically, where the sample contains at least two elements, wherein the method is characterized by placing a sample of known concentrations of known elements in a spectrometer in a first step and measuring the intensity $I1$, $I2$ ... $In$ of the different elements included in the sample, by relating known concentrations $C1$, $C2$ ... $Cn$ for the elements included in the sample to the measured intensities $I1$, $I2$ ... $In$ in a second step such as to calculate a fictive intensity for a 100%-pure element for each of the elements included; calculating calibration constants $K1$, $K2$ ... $Kn$ for each of the elements as the relationship between measured intensity $I1$, $I2$ ... $In$ and the calculated intensity of respective 100%-pure elements in a third step; placing a sample of unknown concentrations of said elements in the spectrometer and reading-off the intensity of the different elements in a fourth step; and in a fifth step calculating the concentration of respective elements in the last mentioned sample as the measured intensity multiplied by respective calibration constants for the elements present in the sample.

BRIEF DESCRIPTION OF THE DRAWINGS

The present invention will be described in more detail below, partly with reference to a table illustrated in FIG. 1.

DETAILED DESCRIPTION OF THE PREFERRED EMBODIMENTS

The present invention is unique in so much that only one sample containing the elements to be calibrated is required for the calibration of two or more elements.

In addition to knowing the concentrations of the elements present in the single sample produced, the method is also based on the ability to simultaneously calculate the background of the sample from solely one single measurement of the sample, i.e. solely one measurement per element, i.e. one point.

There is given below an example with a starting point from the above mentioned as to how two such standards (FE1001 and SI1001) can be calibrated. As will be seen from FIG. 1, line 1, there remains FE1001 that contains 100% $Fe_2O_3$. SI1001 contains 100% $SiO_2$, see line 2 in FIG. 1.

This is used for determining the composition of a sample containing the two elements FESI, see FIG. 1, line 4.

In the MultiScat program that has been used and that is based on the J. E. Fernández algorithms mentioned above, there has been developed a method of calculating the calibration constants for the elements concerned, i.e. for Fe and Si. This process is carried out with the estimated concentrations and the measured intensities of the FESI-sample, whereafter new calibration constants were calculated. The concentrations of the two 100% samples were then calculated with the aid of these constants.

As will be evident from FIG. 1, these concentrations differed slightly from 100% but lie within the accuracy that can be expected with regard to carrying out the measurements concerned.

According to one preferred embodiment the calculation according to the above mentioned second step is carried out by using a relationship between the concentration of an element and the intensity to which the concentration gives rise in the spectrometer used.

According to one preferred embodiment of the embodiment just mentioned, the calculation is carried out in the mentioned second step, in which the known concentrations $C1$, $C2$ ... $Cn$ for the elements present are related to the measured intensities $I1$, $I2$ ... $In$ so that a fictive intensity for a 100%-pure element for each of the elements is established with the aid of algorithms described in the article "Application of J. E. Fernández algorithms in the evaluation of X-ray intensities measured on fused glass discs for a set of international standards and a proposed calibration procedure", J. Malmqvist; X-RAY SPECTROMETRY; X-Ray Spectrom 2001; 30:83-92.

In the above mentioned first step a sample of known concentrations of known elements is placed in an appropriate spectrometer and the intensity I1, I2 . . . In of the sample is measured with respect to the various elements present in the sample.

The above example concerns the calibration of Fe and Si for two standards, FE1001 and SI1001, which were produced with pure chemicals and contained 100% $SiO_2$ and 100% $Fe_2O_3$ respectively. The FESI-sample comprised a mixture of the two oxides.

It is pointed out that the inventive method is in no way restricted to the elements mentioned but that the invention can be applied for analysing all sorts of elements.

In the second step mentioned above, the known concentrations C1, C2 . . . Cn of the elements present in the sample are related to the measured intensities I1, I2 . . . In such as to calculate a fictive intensity for a 100%-pure element for each of the elements present.

The concentration of an element in a sample is determined generally by the relationship $$C_i = k_i \cdot I_i \cdot M, \quad (1)$$

where $C_i$=the concentration of the element i, $k_i$=the calibration constant, $I_i$=the measured intensity and M is the mathematical correction used in accordance with the present invention.

The expected theoretical intensity value in the case of a concentration of 100% in respect of the element E1 is designated $I_{E1\,100\%\ Teor}$. This can be considered to indicate the subquantity of photons registered for the element of all the photons produced with the X-ray tube used in the spectrometer. There is made in step 1 an adjustment, calibration, in which the $I_{E1\,100\%\ Teor}$-value of the elements Fe and Si is adjusted so that the concentrations of the samples will be 100%.

In the third step mentioned above calibration constants K1, K2 . . . Kn is calculated for each of the elements as the relationship between the measured intensity I1, I2 . . . In and the calculated intensity for respective 100%-pure elements.

With the calibration constant defined as $k_{E1}=I_{E1\,100\%\ Teor}/I_{E1\,M\ddot{a}tt}$ the concentration of E1 is obtained by using the algorithm in step 1 for the element E1 at a 100% concentration.

$$C_{E1\,100\%} = k_{E1} \cdot I_{E1\,M\ddot{a}tt} \cdot M$$

With $k_{E1}$ inserted there is obtained $C_{E1\,100\%}=IE1\,100\%\ Teor \cdot M$, where $I_{E1\,100\%\ Teor}$ represents the new transformed calibration constant.

With the new transformed calibration constant inserted in (1) there is now obtained the general relationship $$C_{E1i} = I_{E1\,100\%\ Teor} \cdot I_i \cdot M, \quad (2)$$

In the fourth step mentioned above a sample that includes unknown concentrations of said element is placed in the spectrometer and the intensity of the various elements is read off.

With the aid of the two obtained calibration constants $I_{FeA\,100\%\ Teor}$ and $I_{SiA\,100\%\ Teor}$ the concentrations of Fe and Si are calculated with respect to the FESI-sample, see FIG. 1, line 4.

In a fifth step the concentration of respective elements in the sample last mentioned is calculated as the measured intensity multiplied by a respective calibration constant with respect to the elements present in the sample.

With the aid of the calibration constants, the concentrations with respect to the two samples FE1001 and SI1001 are calculated, the result of this calculation being evident from FIG. 1, lines 6 and 7.

According to a preferred embodiment applied when further samples that contain the same elements as an analysed sample are to be analysed, the fifth step is repeated without repeating the first, second and third steps.

The benefits afforded by the proposed calibrating process are described below.

However, the example given illustrates how calibration with respect to several elements can be achieved with the aid of solely one sample. This is of particular significance in respect of multi-element analysis, of which X-ray fluorescence analysis is often an example where it may concern the calibration of perhaps 10-50 elements with respect to an analysis method. It will readily be understood that the novel process is time saving and that one of the reasons for this lies in the ability of the process to calculate a background with the use of solely one measurement, i.e. the determination of solely one point/element.

The inventive process can also be applied in the validation of an analysis method. With the aid of the inventive process individual especially produced samples used for the calibration process can also be tied to an earlier executed validation of an analysis method, which is beneficial per se as an updating of a validation that can be applied to this individual sample. This is particularly significant in those cases where problems occur with the instrument hardware, such as when changing X-ray tubes, faulty detectors, malfunctioning of a scanner, or other serious faults in the system.

Although the invention has been described with reference to a number of embodiments it will be understood that the inventive process is not strictly bound to the aforesaid algorithms but that other modified algorithms can be used without departing from the scope of the invention described in the accompanying claims.

The present invention shall not therefore be considered restricted to the embodiments described above, since variations and modifications can be made within the scope of the accompanying claims.

The invention claimed is:

1. An X-ray fluorescence method for a composition analysis of a sample containing at least two elements, comprising:
   a first step of placing a first sample of known concentrations of two or more known elements in a X-ray fluorescence spectrometer;
   a second step of measuring an intensity I1, I2 . . . In of each element of the first sample by relating known concentrations C1, C2 . . . Cn for the elements of the first sample to measured intensities I1, I2 . . . In to calculate a fictive intensity for a 100%—pure element for each of the elements of the first sample;

a third step of calculating calibration constants K1, K2 . . . Kn for each of the elements as a relationship between the measured intensity I1, I2 . . . In and the calculated fictive intensity of respective 100%-pure elements;

a fourth step of placing a second sample of unknown concentrations of said elements in the X-ray fluorescence spectrometer and reading-off an intensity of the different elements; and a fifth step of calculating a concentration of respective elements in the second sample as the measured intensity multiplied by respective calibration constants for the elements present in the second sample.

2. The method according to claim 1, wherein the calculation of the second step is carried out by using a relationship between the concentration of an element and the intensity of the concentration given in the X-ray fluorescence spectrometer.

3. The method according to claim 1, wherein the fifth step is repeated without repeating the first, second and third steps when further samples containing the same elements as in said first sample are analyzed.

4. The method according to claim 2, wherein the fifth step is repeated without repeating the first, second and third steps when further samples containing the same elements as in said first sample are analyzed.

* * * * *

UNITED STATES PATENT AND TRADEMARK OFFICE
CERTIFICATE OF CORRECTION

| | | |
|---|---|---|
| PATENT NO. | : 8,119,415 B2 | Page 1 of 1 |
| APPLICATION NO. | : 12/298685 | |
| DATED | : February 21, 2012 | |
| INVENTOR(S) | : Lars Kumbrandt et al. | |

It is certified that error appears in the above-identified patent and that said Letters Patent is hereby corrected as shown below:

On the title page, please amend Item (22) to read as follows:

-- (22) PCT Filed: Apr. 12, 2007 --

Signed and Sealed this
Twenty-fifth Day of September, 2012

David J. Kappos
*Director of the United States Patent and Trademark Office*